United States Patent [19]
Ellis

[11] 4,030,119
[45] June 14, 1977

[54] VIDEO WINDOW CONTROL

[75] Inventor: George W. Ellis, Burnt Hills, N.Y.

[73] Assignee: General Electric Company, Schenectady, N.Y.

[22] Filed: Oct. 1, 1975

[21] Appl. No.: 618,682

[52] U.S. Cl. .............................. 358/11; 358/160; 340/347 AD
[51] Int. Cl.² ................... H04N 7/18; H03K 13/08
[58] Field of Search ......... 178/6.8, DIG. 5, DIG. 8; 340/347 AD; 324/96, 115

[56] References Cited
UNITED STATES PATENTS

| 3,646,586 | 2/1972 | Kurz | 340/347 AD |
| 3,778,614 | 12/1973 | Hounsfield | 250/362 |
| 3,798,366 | 3/1974 | Hunt | 178/6.8 |
| 3,954,098 | 5/1976 | Dick | 128/2.05 Z |

Primary Examiner—Howard W. Britton
Attorney, Agent, or Firm—Jack E. Haken; Joseph T. Cohen; Jerome C. Squillaro

[57] ABSTRACT

An analog signal processor is connected between a refresh memory at the output of the digital computer in an X-ray tomography system and a cathode ray tube display to provide a high resolution gray scale display of a selected portion from an analog signal having wide dynamic range.

14 Claims, 5 Drawing Figures

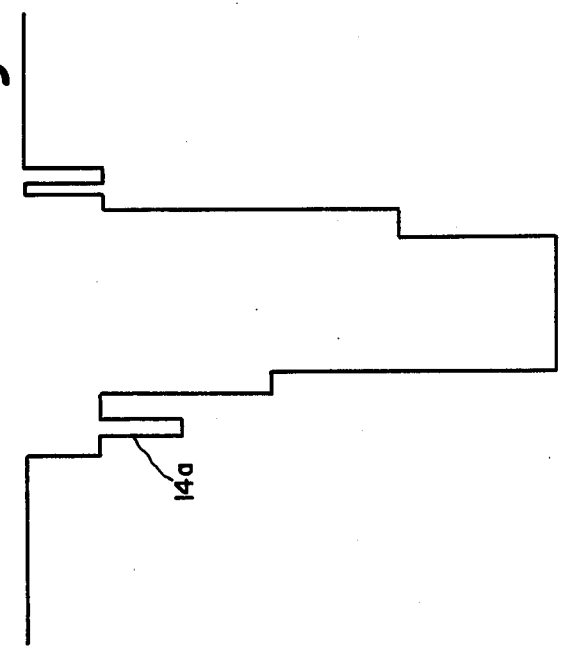
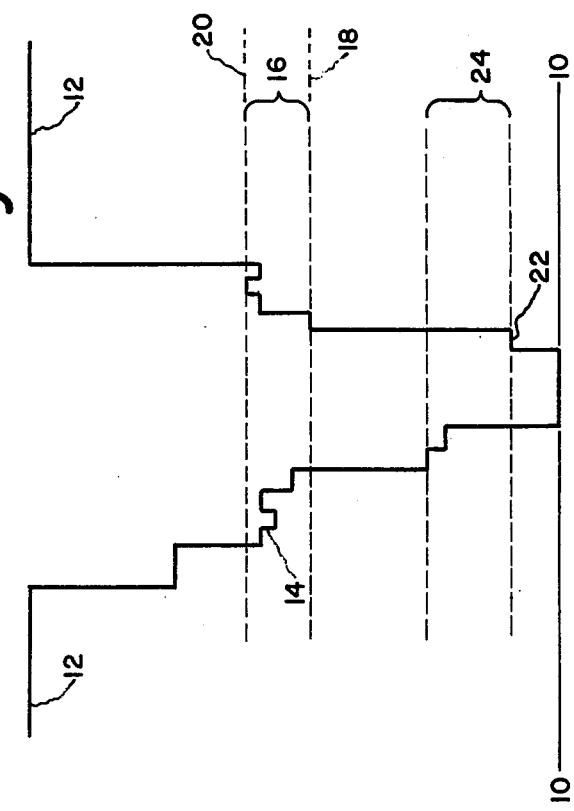
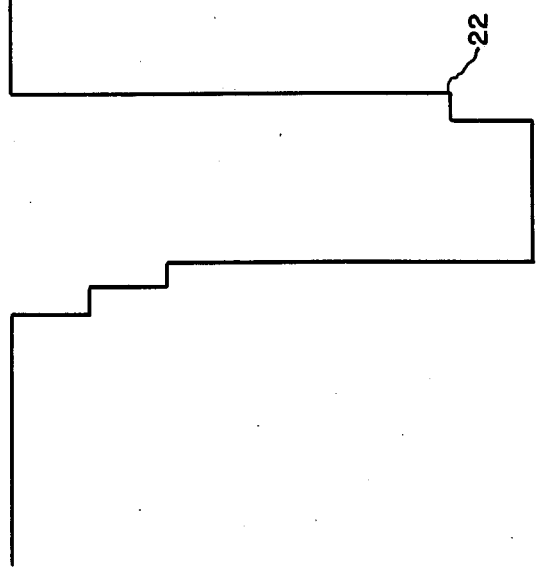

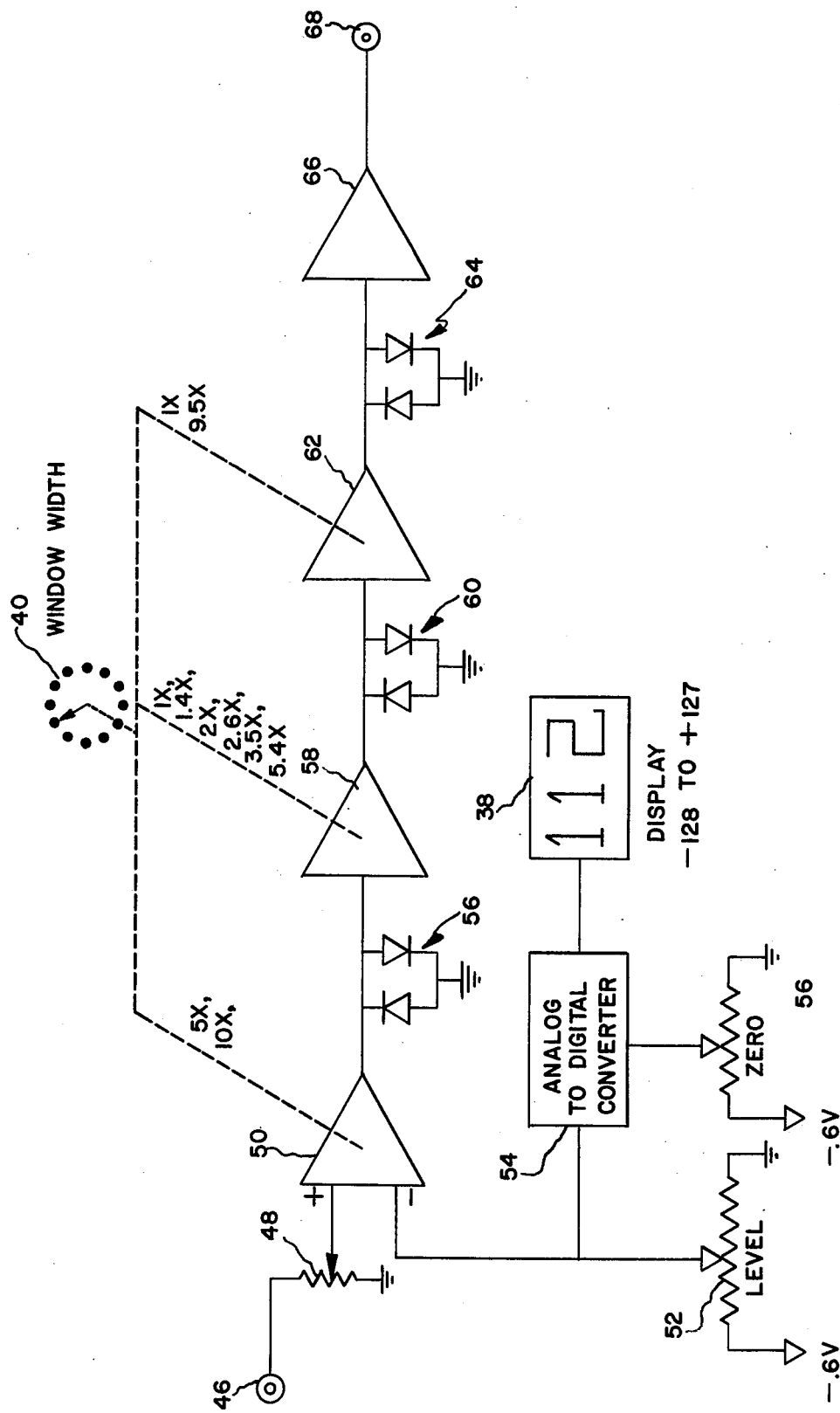

VIDEO WINDOW CONTROL

BACKGROUND OF THE INVENTION

This invention relates to the display of digital data. More specifically, this invention relates to apparatus for increasing the dynamic range in a cathode ray tube display of X-ray tomographic images.

Photographic displays of X-ray absorption characteristics have, for over half a century, been a principal tool for medical diagnosis. Variations in the density of a silver image on a photographic transparency are utilized to represent the X-ray absorption characteristics of internal body tissues. Conventional X-ray photography is, however, limited to the display of superimposed shadows of bodily organs lying in a transmission path. The characteristics of silver halide photographic emulsions tend to limit the X-ray absorption density resolution of images so displayed.

More recently, a method of X-ray tomography has been utilized to provide high resolution, sectional displays of internal tissue structures. In accordance with this method, X-ray transmission characteristics are measured along a plurality of paths through an object undergoing examination. Images of X-ray absorption densities within the object are then constructed by computations on the X-ray transmission data. The calculations are most advantageously performed in a digital computer and the images may be displayed, for example, on a cathode ray tube. A specific method of X-ray tomographic imaging is, for example, described in U.S. Pat. No. 3,778,614 to Hounsfield, which is incorporated by reference, as background material in this disclosure.

X-ray tomographic methods are capable of producing images having far greater absorption density resolution than images produced by photographic techniques. For example, present tomographic image reconstruction methods are capable of quantitizing X-ray absorbtion density measurements into 256 or more separate levels. Cathode ray tube data displays are incapable, however, of displaying more than approximately 15 distinct gray-scale levels.

Significant medical information, for example, the presence of tumors in soft tissue, is often represented by minimal level changes in tomographic image density. The detection of such level changes is often accomplished by a process wherein a radiologist views a computer-generated image having a limited gray-scale range and, on the basis of his observation and experience, interactively modifies the computer program to present significant density information within the dynamic range of the image display. The observations and procedures inherent in this process are, of course, highly subjective so that a lengthy series of iterations may be required to obtain an optimum display. Each modification to the computer program will, in general, cause an interruption in the processing of other tomographic image information and, by distracting the radiologist's attention from the display screen will lengthen the image interpretation process.

It is often useful to determine the absolute X-ray absorption density displayed in a tomographic image. If the output signal of a digital computer has been modified to optimize a cathode ray tube display, such absolute density measurements may require further calculations to recover the absolute density information.

SUMMARY OF THE INVENTION

In accordance with the present invention, I provide an analog processor unit for connection between the video output of a digital computer and the input of a cathode ray tube display. The analog processor, which may be disposed adjacent to the cathode ray tube, allows display of an analog signal having a dynamic resolution which may be selected from any subrange within an analog signal having wide dynamic range. A radiologist may, by use of the processor, interactively select and modify the center level and dynamic range of a cathode ray tube display to most advantageously view high resolution data. The processor operates upon an analog output which is generated from digital data and may, therefore, accomplish modification of a displayed image without program changes or additional computer time processing. The video signal level which is selected as a center level by the processor unit is a linear function of the absolute X-ray density in the image and may, therefore, be measured and digitized to provide a readout of the absolute value of the base level pictured in the display. The center level of the display and the dynamic range may be fed back from the analog processor into an input of the computer and displayed on the cathode ray tube face for photographic recording.

It is, therefore, an object of this invention to provide interactive, analog means for adjusting the center level and dynamic range of a cathode ray tube display.

It is another object of this invention to reduce the digital processor time required for the display and interpretation of tomographic X-ray images.

BRIEF DESCRIPTION OF THE DRAWINGS

The novel features believed characteristic of the present invention are set forth in the appended claims. The invention itself, together with further objects and advantages thereof, may be best understood with reference to the following detailed description, taken in connection with the appended drawings in which:

FIG. 1 is an example of a high resolution analog signal output from a tomographic image computer;

FIGS. 2 and 3 are output signals from an analog processor which have been generated from the signal of FIG. 1 to provide optimum cathode ray tube data displays;

FIG. 5 is a simplified schematic diagram of the analog processor of the present invention.

DESCRIPTION OF THE PREFERRED EMBODIMENT

Figure 4:
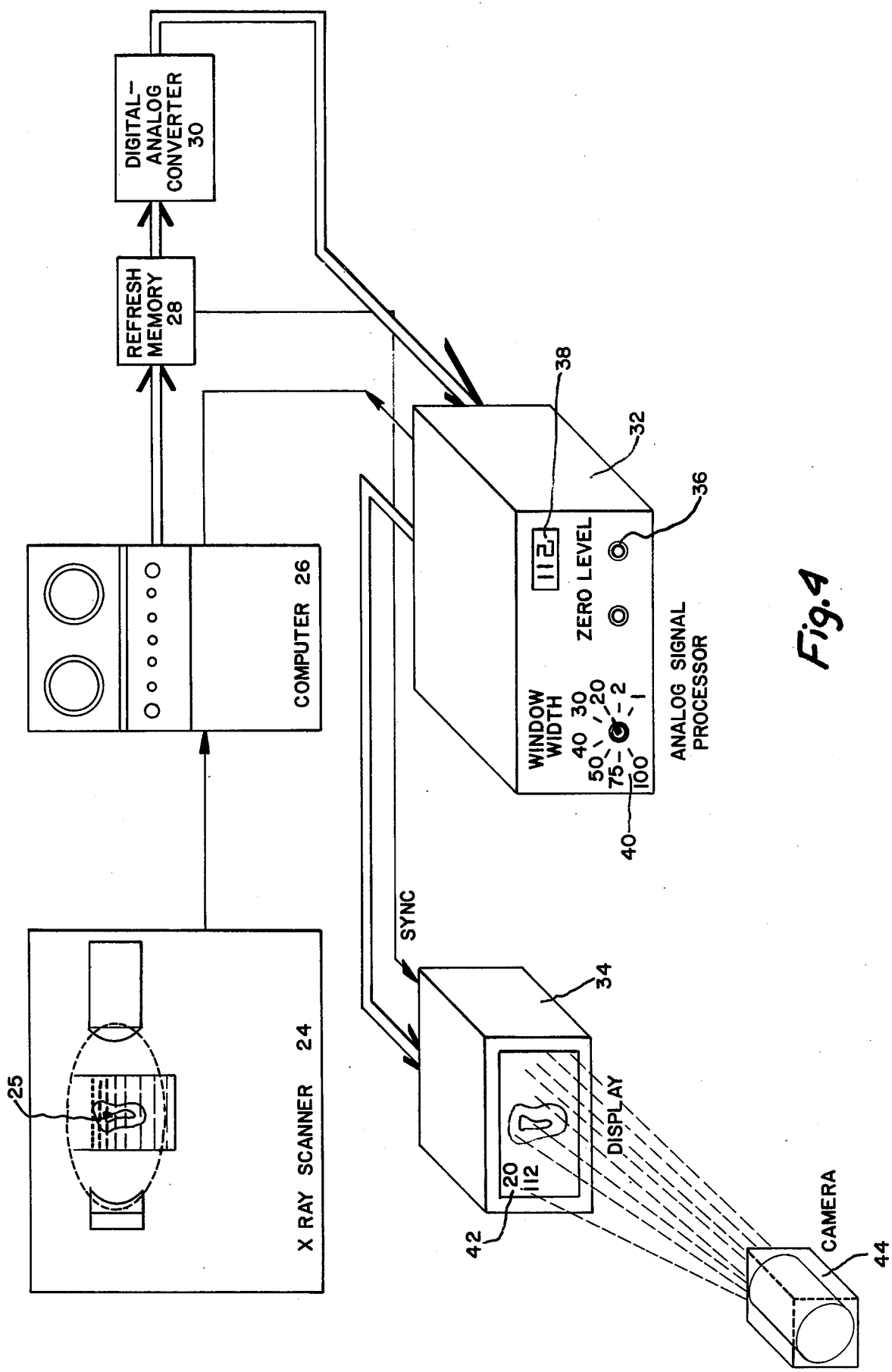
FIG. 4 is a tomographic imaging system incorporating the processor of the present invention.

Tomographic X-ray image information is generally generated from X-ray detector signals by the solution of large numbers of simultaneous equations in a digital computer. The output signal of the computer represents a matrix wherein each element is a numerical value of X-ray absorption density over a particular discrete area (pixel) in an image plane. X-ray tomographic systems are capable of resolving small differences of X-ray absorption density and are therefore extremely useful, for example, in the detection of soft tissue tumors. The X-ray absorption density resolution of a given system is a function of the X-ray dosage administered to a patient and the computation time utilized for construction of the image. Present tomographic measurement systems typically resolve 256 or more discrete levels of X-ray absorption density.

The image signal generated by the computer is most advantageously stored in digital form in a refresh-buffer memory, the contents of which are serially scanned and converted into analog form for presentation to the intensity modulation input of a cathode ray tube. Such an analog signal generally carries far more density information than may be displayed on a cathode ray tube which may, for example, be limited to resolving approximately 15 intensity levels. It has been found, however, that significant medical information is often represented by minimal changes within an analog signal having a large dynamic range.

FIG. 1 schematically represents a portion of an analog image signal which might, typically, be generated from the output of a computer buffer memory. The signal covers a wide dynamic range wherein minimum density levels 10 may, for example, represent voids and maximum signal levels 12 may, for example, represent dense bone or metal objects. Small variations 14 within the signal waveform, which may represent 1/256 or less of the total dynamic signal, often contains significant medical information which might, for example, indicate the presence of tumors or other lesions. The limited gray-scale of a cathode ray tube display would, however, obscure the presence of the variations 14 in the entire dynamic range of the signal of FIG. 1 were displayed on a cathode ray tube.

In accordance with the present invention, I provide an analog processor wherein a small portion or window extracted from within the larger dynamic range of a signal may be expanded to fill the gray-scale of a cathode ray tube. The center level and width of the window with relation to the overall signal envelope may be adjusted to provide an optimum cathode ray tube display. For example, if a signal within the dynamic range of the window 16 of FIG. 1 is expanded to fill the gray-scale range of a cathode ray tube, the signal of FIG. 2 results. All signal levels below the base level 18 of the window 16 are displayed at the minimum cathode ray tube intensity whereas all signal levels above the maximum threshold level 20 of the window 16 are displayed at maximum cathode ray tube intensity. Signal levels falling within the window 16 are expanded to fill the dynamic range of the cathode ray tube. The small signal variation 14 of FIG. 1 is thereby expanded to the large dynamic variation 14a of FIG. 2 and will thereby be made visible on a cathode ray tube display.

The position of the window 16 may be adjusted to provide high resolution displays from various portions of the overall signal envelope. Thus, the variations 22 in the lower portion of the waveform of FIG. 1 may be expanded, for example, by adjustment of the window parameters to the range 24 so as to produce the output waveform of FIG. 3.

FIG. 4 schematically illustrates a typical X-ray tomography system incorporating the present invention. An X-ray scanner 24 produces electrical output signals corresponding to the X-ray absorption characteristics along a plurality of transmission paths through an object 25. The output signals from scanner 24 are applied at the inputs of a digital computer 26 wherein well-known computational algorithms are applied to produce digital matrix signals corresponding to a sectional image of X-ray absorption densities within the object 25. The digital matrix signals are transmitted from the computer 26 to a refresh memory 28 where they are stored for transmission to a display. The contents of the refresh memory 28 are sequentially scanned into a digital-analog converter 30 which transforms them into an analog output signal wherein voltage levels correspond to intensity levels in a raster scanned display of the image. The output of the digital-analog converter 30 is applied to the input of an analog signal processor 32 (more fully described below) which selectively expands portions of the analog signal to match the gray-scale range of a cathode ray tube display. The expanded signal produced by the analog signal processor 32 is applied to an intensity modulation input of a cathode ray tube display 34 in conjunction with raster synchronization signals which are generated within the refresh memory 28 in a conventional manner.

The analog signal processor 32 is equipped with a level control 36 which permits the operator to adjust the value of a voltage level in the analog signal corresponding to the center level (medium gray level) presented on the display 34. The value of the digital signal which corresponds to that center gray scale level is displayed on a digital readout 38 at the analog signal processor 32. The window width (range of the analog signal levels presented on the gray scale of the display 34) is likewise adjustable by means of a window width control 40 at the analog signal processor 32.

Under the control of the digital computer 26, X-ray image information is transferred to the refresh memory 28 and presented on the cathode ray tube display 34. A radiologist or tomograph operator manipulates the controls of the analog signal processor 32 to most advantageously display medically significant information on the cathode ray tube screen. The analog signal processor 32 also provides an output signal to the digital computer 26 corresponding to the readings of center level on the digital readout 38 and the setting of the window width control 40. When an optimum display condition is reached, the digital computer may, under program control, provide digital character readouts of the center level and window width which are transmitted through the refresh memory and digital analog converter for presentation in numerical form 42 on the screen of the display 34. The image and numerical information presented on the display 34 may, if desired, then be photographically recorded with a camera 44.

FIG. 5 is a simplified schematic diagram of the analog signal processor 32. The output of the digital analog converter (30 of FIG. 4) is applied to an input jack 46 of the analog signal processor. A potentiometer 48 forms a voltage divider to reduce the voltage of the input signal at the jack 46 to a level compatible with the input of an operational amplifier 50. The output from the wiper of the potentiometer 48 is applied to a positive summing input of the operational amplifier 50. A fixed reference voltage is applied to a level adjustment potentiometer 52 which is operated by the level control (36 of FIG. 4). A signal determined at the wiper of the level control 52 is applied to a negative summing input of the operational amplifier 50 and to the input of an analog-digital converter 54. The analog-digital converter 54 is calibrated to correspond to digital signal levels in the refresh memory (28 of FIG. 4) and produces an output corresponding to the reference signal at the wiper of the level control potentiometer 52. Calibration of the analog-digital converter 54 is facilitated by a zero adjust potentiometer 56 which is controlled from the panel of the analog signal processor 32. The output of the analog-digital converter 54 is displayed on the digital readout 38, which is likewise located on the panel of the analog signal processor 32. The numerical display generated by the analog-digital converter 54 and presented on the digital readout 38 corresponds to the quantitized signal level producing the center level as presented on the cathode ray tube display 34.

The output of the operational amplifier 50 is a signal equal to the difference of the reference level signal produced at the wiper of the potentiometer 52 subtracted from the analog input signal produced at the wiper of the potentiometer 48. The output signal from the amplifier 50 is clipped by a diode pair 56 and further amplified in a cascaded operational amplifier 58. The output of the operational amplifier 58 is again clipped with a second diode pair 60 and applied to the input of a third cascaded operational amplifier 62. The output of the operational amplifier 62 is clipped with a third diode pair 64 and applied to a fourth cascaded operational amplifier 66. The operational amplifier 66 is configured to drive a 75 ohm video output jack 68. The gain of the operational amplifiers 50, 58, and 62 is adjustable by means of the window width control switch 40 to provide an adjustable cascade signal amplification range from approximately 5X to approximately 500X. The gain of the individual amplifier stages is chosen in a well-known manner to provide convenient switching and to prevent overload of any individual amplifier output. By way of example, in a typical system, the input voltage level at the wiper of the potentiometer 48 is approximately 0.6 volts peak to peak. The gain of the operational amplifier 50 is selectable at either 5X or 10X, the gain of the operational amplifier 58 is selectable at either 1X, 1.4X, 2X, 2.6X, 3.5X, or 5.4X. The gain of the operational amplifier 62 is selectable at either 1X or 9.5X and the output video level from the operational amplifier 66 is approximately 1 volt peak to peak into 75 ohms. The diode pairs 56, 60, and 64 are typically selected to clip at approximately 1.2 volts peak to peak. If, in the above-described exemplary configuration, the analog input signal represents 256 discrete density levels. The window width control may be connected to provide window widths of 1 level, 2 levels, 20 levels, 30 levels, 40 levels, 50 levels, 75 levels, or 100 levels. The digital readout may likewise be adjusted to read the value of the center level density over a range corresponding to the 256 discrete density levels.

The analog processor unit may be installed adjacent the cathode ray tube display to permit rapid adjustment by a radiologist whose attention may be continuously directed to the displayed image. The analog signal processor operates on an analog signal generated from a refresh memory to modify a displayed image on a cathode ray tube display and does not require computer processor time or interruption and modification of the precursor computer program to effect display modification.

While the invention has been described in detail herein in accordance with the preferred embodiment thereof, many modifications and changes therein may be effected by those skilled in the art. Accordingly, it is intended by the appended claims to cover all such modifications and changes as fall within the true spirit an scope of this invention.

The invention claimed is:

1. In an X-ray tomographic imaging system of the type comprising:
a source of radiation transmission data, a digital computer connected to receive said transmission data, and to calculate therefrom digital tomographic image data, a digital-to-analog converter connected to receive said digital image data and to produce therefrom a high resolution, analog image waveform, and an image display connected to receive and present a limited resolution analog image signal in an intensity modulated, visual format; the improvement comprising
an analog data processor connected to receive said high resolution image waveform and to convert said waveform into a limited resolution signal comprising an expanded function of those levels of said high resolution image waveform falling within the range of a selectable window function, said data processor including:
means for subtracting a reference level from said high resolution image waveform;
variable gain amplifier means connected to receive and increase the output of said means for subtracting; and
clipping means connected to act upon the output of said variable gain amplifier means whereby high level and low level data from said high resolution analog image waveforms are excluded from said limited resolution signal and the intensity resolution of said image display is selectively increased.

2. The imaging system of claim 1 further comprising means for matching said limited resolution signal to a 75 ohm video transmission system.

3. The imaging system of claim 1 wherein said image display is a cathode ray tube display.

4. The imaging system of claim 1 wherein said analog data processor comprises means for adjusting the magnitude of said reference level and means for measuring the magnitude of said reference level.

5. The imaging system of claim 4 wherein said high resolution analog image waveform is representative of at least 256 discrete intensity levels.

6. The imaging system of claim 5 wherein the output of said means for measuring is a digital signal representative of the value of one of said discrete intensity levels.

7. The imaging system of claim 6 wherein said analog data processor is further connected to display characters representative of the output of said means for measuring said image display.

8. An analog signal processor for connection between a high resolution analog signal source and a cathode ray tube display comprising:
subtracting means connected to receive a high resolution analog video signal and a reference level and for producing an output signal representative of the difference of said reference level subtracted from said video signal;
measuring means connected to receive said reference level and to display digital characters representative of the magnitude of said level;
variable gain amplifier means connected to receive and increase the output signal from said subtracting means;
clipping means connected to limit the dynamic range of said increased signal from said amplifier means; and adjusting means connected to permit selectable determination of the value of said reference signal level and the gain of said amplifier means.

9. The processor of claim 8 wherein said variable gain amplifier means comprise a plurality of cascaded operational amplifiers.

10. The processor of claim 9 wherein said adjusting means are connected to allow adjustment of the gain of said amplifier means to one of a plurality of predetermined values, said predetermined values comprising the values 1X, 2X, 20X, 30X, 40X, 50X, 75X, and 100X.

11. The processor of claim 10 wherein said plurality of operational amplifiers comprise a first operational amplifier configured to provide discrete selectable amplification levels of 5X and 10X; a second operational amplifier configured to provide discrete selectable amplification levels of 1X, 1.4X, 2X, 2.6X, 3.5X, and 5.4X; and a third operational amplifier configured to provide discrete selectable amplification levels of 1X and 9.5X.

12. The processor of claim 10 wherein said clipping means comprise a plurality of diode pairs, each of said diode pairs comprising a first diode having a cathode and an anode and a second diode connected in parallel with said first diode, the cathode of said second diode being connected to the anode of said first diode and the anode of said second diode being connected to the cathode of said first diode.

13. The analog signal processor of claim 12 wherein said first operational amplifier comprises said subtracting means.

14. The signal processor of claim 13 wherein one of said plurality of diode pairs is connected in parallel with the output of each of said operational amplifiers.

* * * * *